United States Patent [19]

McGaughey et al.

[11] Patent Number: 4,487,605

[45] Date of Patent: Dec. 11, 1984

[54] FLASHBACK DEVICE FOR CATHETERS

[75] Inventors: John McGaughey, Tampa; W. Patrick McVay, Clearwater; William Lauer, Valrico, all of Fla.

[73] Assignee: Critikon, Inc., Tampa, Fla.

[21] Appl. No.: 442,389

[22] Filed: Nov. 17, 1982

[51] Int. Cl.³ .............................................. A61M 5/00
[52] U.S. Cl. .................................. 604/168; 604/900; 128/765
[58] Field of Search .............. 604/168, 900; 188/765, 188/767; 251/4, 6, 7, 9; 401/163, 160

[56] References Cited

U.S. PATENT DOCUMENTS

| 1,995,218 | 3/1935 | Osterhout | 401/160 |
| 2,502,866 | 4/1950 | Lust | 401/163 X |
| 3,459,183 | 8/1969 | Ring et al. | 128/767 X |

FOREIGN PATENT DOCUMENTS 6995 of 1903 Denmark .......................... 401/158

Primary Examiner—Stephen C. Pellegrino
Attorney, Agent, or Firm—Audley A. Ciamporcero

[57] ABSTRACT

Negative pressure to accelerate flashback is formed by selective deformation of an elastomeric bladder. The bladder and a next adjacent cam means are enclosed in a housing, penetrated by a slide or roller engaging the cam surface. As the slide or roller moves along the cam surface, the bladder is selectively deformed first to close, then to evacuate distally and then to reopen at a negative differential pressure.

6 Claims, 7 Drawing Figures

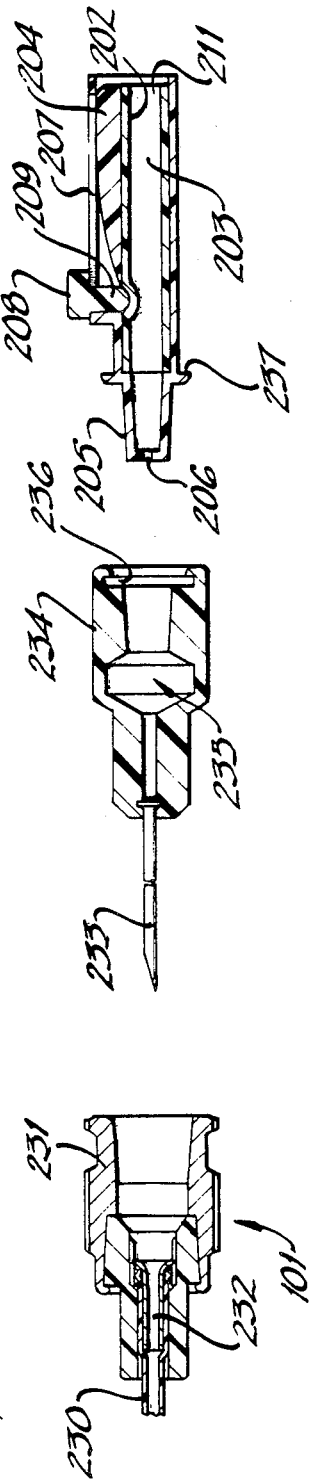
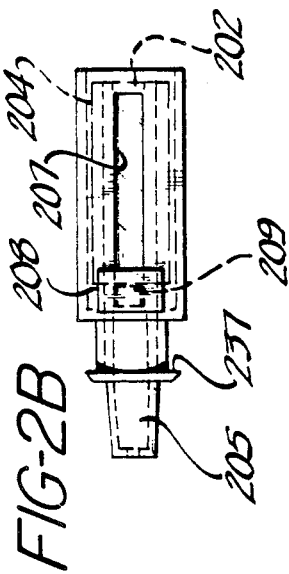
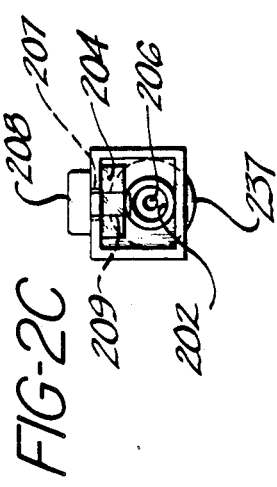
FIG-2A
FIG-2B
FIG-2C

FLASHBACK DEVICE FOR CATHETERS

FIELD OF THE INVENTION

This invention relates to vascular fluid administration devices, and more particularly to apparatus for accelerating blood flashback in intravenous catheters.

BACKGROUND OF THE INVENTION

Direct vascular administration of medicaments and nutritional fluids has become the preferred mode of treatment for substantially all critically ill patients, as well as for numerous patients with chronic conditions. Indwelling intravenous (and occasionally, intra-arterial) catheters have for the most part replaced rigid needles as the preferred vehicle for vascular fluid administration. Catheter markets are generally held to be expanding rapidly, indicating general acceptance through the worldwide medical community; improvements in catheter structure and operation further permit utilization for still further medical applications.

Conventionally, such catheters include an assembly in which a flexible tube, for example of polymeric construction, is bonded to a hub, and the assembly is carried about a removable cannula which extends slightly beyond the extremity of the tube. The catheter is set in place by easing the assembly into the flesh of the patient until it just penetrates the vascular wall. When the device is so set, the cannula is removed, leaving the catheter tube indwelling. Fluid administration sets, pumps, or the like are coupled to the hub, and suitable medicinal or nutritional fluids are delivered to the patient directly into the blood.

Probably the most accepted objective method for determining the proper placement of a catheter is the occurrence of "flashback", or backflow of blood up through the catheter, in some cases into a visible reservoir in the catheter hub. Of course, since the catheter insertion process is often quite swift, it is desirable that the flashback response time be very brief, thereby to give the treating physician or nurse a fast, essentially "real time" indication of the actual position of the catheter tip. Clearly, if the flashback response time is unduly slow, the flashback function will at best be of no use to the treating physician or nurse, and at worst will be totally misleading. For example, it is desirable that the flashback function occur quickly enough to avoid cannula penetration through the back wall of the vasculature and into surrounding tissue.

It is a primary object of the present invention to provide apparatus for accelerating the flashback response time in intravascular catheters.

One method, to which the principles of the present invention ultimately relate, for accelerating flashback response time, is to create a slight vacuum in a flashback chamber within the catheter hub, thereby to accelerate the flow of blood back through the cannula for indication of proper placement. Often, this is done by means of a syringe, which is coupled to the catheter, and which creates a negative pressure differential as the plunger is withdrawn. Of course, in creating the partial vacuum, it is necessary to insure that air emboli or the like are not forced through the catheter and into the vascular system of the patient. It is likewise important that the partial vacuum be as slight as possible while being effective, lest vascular collapse or tissue withdrawal be accidently caused.

It is accordingly a further object of the present invention to provide a device for accelerated flashback response time safely utilizing the vacuum pull method, while avoiding the risk of unintentional deposit of fluid, air, or the like undesirable foreign substances into the blood stream.

CROSS REFERENCE TO RELATED APPLICATIONS

Reference is made to concurrently filed, copending application U.S. Ser. No. 442,388, entitled IMPROVED FLASHBACK DEVICE FOR CATHETERS, which also relates to acceleration of flashback.

SUMMARY OF THE INVENTION

In accordance with the principles of the present invention, an elastomeric bladder is either included in, or coupled to the catheter needle, and forced to create a partial vacuum through application of compressive force by a next adjacent cam means. In particular, the cam surfaces are so configured as to provide deformation of the bladder selectively when a next adjacent actuating roller is moved along the cam surface. In the normal, or undeformed state, the cam rests alongside the bladder but is essentially uncoupled from the actuator (i.e., slide, roller, or the like). As the actuator is moved to meet the cam and ride along the camming surface, the cam is forced downwardly into the bladder, first forming compressive closure on a proximate end thereof, and thereafter successively to be closed distally as the bladder is evacuated from a vented distal end. As the bladder is evacuated and closed, further movement of the cam actuator, in conjunction with the elastomeric recovery force of the bladder itself, causes the bladder to remain sealably closed at the distal extremity, but to reopen at points proximate thereto. In turn, a negative differential pressure is set up between the catheter and the bladder. Correspondingly, as the catheter becomes positioned properly within the vein (or, less commonly, artery) of the patient, blood is drawn in accelerated fashion by the negative pressure differential back up and into the flashback chamber, indicating substantially and instantaneously to the user that the catheter is properly placed.

It is a feature of the present invention that a partial vacuum of safe magnitude is set up without substantial danger of introduction of air emboli into the vascular system. In particular, the first cam actuated closure of the bladder tends to isolate the catheter and the patient from the bladder evacuation process, and once this is completed, the proximal reopening of the bladder creates a safe pull on the flashback chamber.

DESCRIPTION OF THE DRAWINGS

FIGS. 2A through 2C show various views of an illustrative embodiment incorporation of the principles of the present invention together with a conventional catheter set up.

BEST MODE FOR CARRYING OUT THE INVENTION

Figure 1A:
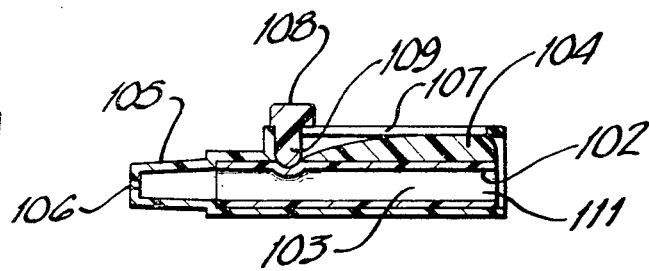
FIGS. 1A through 1D show, in cutaway side profile, operation of a preferred embodiment of the principles of the present invention.

Referring first to FIGS. 1A through 1D, there is shown a preferred embodiment of the principles of the present invention. As will be noted, FIGS. 1A through 1D represent a series of views illustrating successive operation in accordance with the principles of the present invention. That is, considering the embodiment respectively from FIG. 1A, which is the fully relaxed, equalized pressure position, to FIG. 1D, which is the position in which a negative differential has been created relative to the catheter (not shown), like parts receive like numbers.

A housing 101 is shown having a luer taper 105 at a proximate end, which is adapted to be connected to a catheter, for example to the housing which carries the catheter needle. A vent 106, for example a slot, hole, or plug of porous material, permits the interior 103 of the apparatus to communicate with the catheter, not shown in detail, and in turn, when the catheter needle is correctly placed, with the vein of the patient. Within the housing 101, and in fact defining the chamber 103, is a bladder 102, advantageously constituted of elastomeric tubing. An elongated cam 104 is carried alongside the bladder 102, advantageously in relatively close fit between bladder 102 and the housing 101 when the apparatus is in the relaxed position shown in FIG. 1A. A slot 107 is formed in the top portion of the housing 101, and is penetrated by a cam actuator 108 and 109. In particular, the actuator includes an exterior portion 108 adapted to be manipulated by the user, and a slide or roller portion 109 adapted, when the actuator is so manipulated, to ride on the camming surface of the cam 104, in turn to deflect the cam 14 into the bladder 102. In particular, the embodiment of FIGS. 1A through 1D employ a slide arrangement wherein the actuator 108 and 109 may be moved back and forth along the slot 107 in housing 101.

In the drawing, it will be noted that the cam 104 has a cross section much like an air foil, with an essentially flat lower surface conforming to or contacting the bladder 102, and a top camming surface, which, in conjunction with the actuator 108 and 109, controls the degree and nature of deflection of the bladder 102 by the cam 104.

In FIG. 1A, the bladder is essentially fully opened, the actuator is at the left most (i.e., proximate) side of the slot 107, and the cam 104 is maintained through the outward spring force of the bladder 102 in the position shown, against the upper surface of the housing 101. In the figures, although no catheter is shown, it is assumed that the luer taper 105 is in fact connected to a catheter of conventional construction, and that the vent 106 with chamber 103, in fact either communicates with or actually constitutes, the flashback chamber of such a catheter.

Figure 1B:
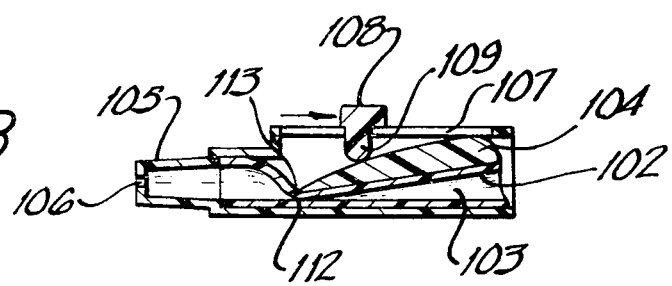

FIG. 1B shows an interim view wherein the cam actuator 108 and 109 has been moved somewhat distally, causing the slide or roller portion 109 to ride along the top portion of the cam 104. Since the air foil cross sectional configuration of the cam 104 causes the cam 104 thereby to be forced downwardly, there also occurs a corresponding compression of the bladder 102, and closure of the chamber 103 at the most proximal point 113 of the cam 104. At the point shown in FIG. 1B, the cam actuator 108 and 109 has been moved distally to the point at which the proximate extremity 113 of the cam 104 has forced the bladder 102 to be closed against itself and the lower surface of the housing 101, thereby dividing the chamber 103 into two parts, the proximate part still communicating with and being at the same pressure as the catheter.

Figure 1C:
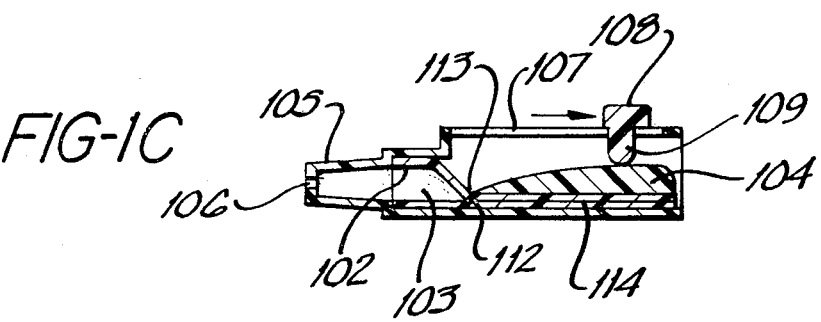

Noting that the bladder 102 is vented at a distal extremity 111, (either by an open vent or by a closed reservoir) reference to FIG. 1C demonstrates that still further distal movement of the actuator 108 and 109, thereby contacting higher and higher portions of the air foil cross section of the cam 104, causes the cam 104 to pivot about the proximate extremity 113, venting the bladder distally through 111, and causing closure of the bladder through the distal extent 114 of the bladder under compression by the cam 104. During this phase of operation, the proximate portion of the chamber 103 is still communicating with and is at equalized pressure with the catheter.

Figure 1D:
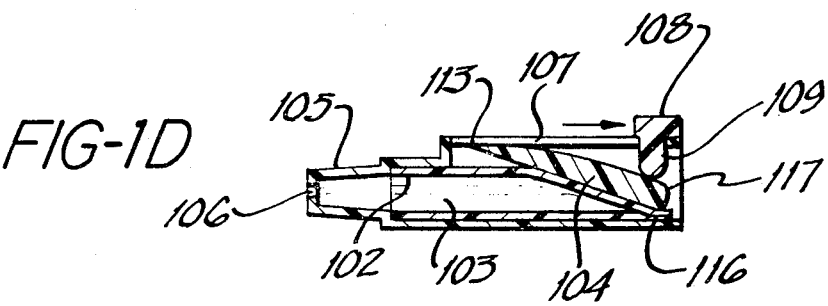

As noted in FIG. 1D, still further distal movement of the cam actuator 108 and 109 causes the slide/roller portion 109 to move past the peak point of the air foil cross section of cam 104, thereby somewhat to lessen the compressive pressure over the entire length of the cam 104, but to maintain that pressure at a distal extremity 116 of the cam 104. This action relieves the proximate pressure on the cam 104, and the recovery force of the bladder 102 pushes the proximate segments of the cam 104 upwardly, while the sealed compressive engagement of the distal extremity of the bladder 102 is maintained at point 116 by the distal extremity of the cam 104 pressing downwardly against the housing 101. This reopening of the cavity 103 brings on a correspondingly increased volume communicating through the vent 106 with the catheter, which volume can only be satisfied through the catheter itself. Therefore, so long as the tip of the catheter needle is embedded either in the flesh or the vasculature of the patient, such reopening of the chamber 103 corresponds to exertion of a negative differential pressure, or pull on the catheter. Substantially instantaneously as the catheter needle penetrates the vasculature of the patient, this negative pressure differential pulls blood back up through the catheter and into the flashback chamber. The user thereby is in a position to determine that the catheter has been properly placed, and may proceed in conventional fashion to remove the needle, leaving the catheter tube indwelling for use as desired.

While FIGS. 1A through 1D show a more or less stylized embodiment of the principles of the present invention, FIGS. 2A, 2B, and 2C show a somewhat more specific version, adapted to be coupled to a catheter. In particular, FIG. 2A shows a cross-section of a typical catheter, and an embodiment of the principles of the present invention; FIG. 2B shows a top plan view of the apparatus in accordance with the principles of the present invention; and FIG. 2C shows an end view of the same apparatus.

In FIG. 2A, the catheter segment is defined by a hub 231, to which a catheter tube 230 is affixed by means of an eyelet 232, which resides within the tube 230 and creates outward pressure for a force fit of the tube 230 in the hub 231. A central chamber is adapted to receive the needle mechanism, including needle hub 234 and the needle itself 233. In operation, the needle hub 234 resides in the cavity of the catheter hub 231, with the needle 233 extending through the catheter tube 230 and penetrating slightly outwardly therefrom. Within the needle hub 234 is a chamber 235, advantageously useful as a flashback chamber, provided the hub 234 includes at least a portion which is transparent or translucent to show the presence of blood in the cavity 235.

The FIG. 2A drawing shows the differential flashback accelerator embodying the principles of the present invention being distinct from and connectable to the needle hub 234 by means of a snap fit. Quite clearly, depending upon the desire of the designer, these two parts could as easily be fabricated as a single part, or could be connectable by a variety of other known mechanisms, such as a luer connection.

As will be noted from FIGS. 2A, 2B, and 2C, essentially embodying the principles of the present invention, the tubular elastomeric bladder 202 is coupled, as desired, to the proximate end of the evacuating unit, and a protective surrounding wall carries a slot 207 at the top thereof. In turn, the slot 207 engages a side or roller mechanism 208 and 209, in turn controlling the pressure of a cam 204 against the bladder 202. The elements in FIGS. 2A through 2C function the same as do their structural and functional analogs shown in FIGS. 1A through 1D, and described hereinbefore.

It is understood that the foregoing sets forth preferred and illustrative embodiments of the principles of the present invention, but that numerous alternative embodiments could likewise be employed without departure from the spirit or scope of the present invention. For example, the selection of materials useful in accordance with the principles of the present invention provides extensive freedom to the designer. The elastomeric bladder material 202 may be freely chosen, as may the materials for the cam surface and enclosure, so long as the cam and the surrounding structure are substantially rigid relative to the elastomeric bladder. The particular shape of the camming surface is less critical than is its function, of first sealing the bladder, then evacuating it distally, then sealing it distally and reopening it proximally to create a negative differential pressure. It is likewise to be noted that although the principles of the present invention, and the embodiments thereof, are set only in terms of vascular flashback function, they will no doubt enjoy a substantial equivalent application to a variety of otherwise conventional fluid aspiration applications.

What is claimed is:

1. In a vascular fluid administration or withdrawal device, apparatus for indicating desired placement of said device through the mechanism of flashback comprising:
   (a) an elastomeric bladder defining a chamber, open on a distal end and communicating with said device on a proximate end;
   (b) an elongated cam means adjacent said bladder, tapering in thickness from said distal end to said proximate end; and
   (c) actuator means, slidably movable between said proximate and said distal ends, and adapted to urge said cam means to deform said bladder, progressive distal movement of said actuator means causing respective proximate closure, distal evacuation, and distal closure of said bladder.

2. Apparatus as described in claim 1 wherein said taper is formed between two opposing surfaces, one of which is substantially flat and the other of which has a predetermined curvature, said curvature establishing the degree of taper and hence the relative correspondence between the position of said actuator means and the closure condition of said bladder.

3. Apparatus as described in claim 2 and further comprising:
   a slotted housing enclosing said bladder and said cam means; wherein said means for actuating penetrates said slot for external manipulation, manipulation of said means for actuating along said slot causing said cam to deform said bladder in accordance with said predetermined curvature.

4. Apparatus as described in claim 3 wherein said means for actuating comprises a roller engaging said curvature.

5. Apparatus as described in claim 3 wherein said means for actuating comprises a slide means engaging said curvature.

6. Apparatus as described in claim 2 and sequentially operable, in response to deformation of said bladder by said cam means under control of said means for actuating, in the sequence of:
   (a) said bladder being undeformed, said cam means being next adjacent;
   (b) an end of said cam means proximate said device pressed by said means for actuating to deform and close a proximate section of said bladder;
   (c) said proximate end of said cam means maintaining said closure as said cam means further compresses and evacuates parts of said bladder distal to said closed proximate section;
   (d) said bladder closed and evacuated at points distal to said closed proximate section; and
   (e) a distal end of said cam means pressed in sealable closure of a distal extremity of said bladder as proximate portions of said cam means release compressive force on said bladder, thereby creating a negative differential pressure against said device.

* * * * *